(12) United States Patent
Tallentire et al.

(10) Patent No.: US 6,463,815 B1
(45) Date of Patent: Oct. 15, 2002

(54) GAS SAMPLING ASSEMBLIES

(75) Inventors: Alan Tallentire, Wilmslow (GB); Colin Samuel Sinclair, Manchester (GB)

(73) Assignee: Air Dispersions Ltd, Manchester (GB)

( * ) Notice: Subject to any disclaimer, the term of this patent is extended or adjusted under 35 U.S.C. 154(b) by 0 days.

(21) Appl. No.: 09/589,100

(22) Filed: Jun. 8, 2000

(30) Foreign Application Priority Data

Jun. 9, 1999 (GB) ............................................. 9913445

(51) Int. Cl.[7] .................................................. G01N 1/22
(52) U.S. Cl. .................................................. 73/863.23
(58) Field of Search ............................. 73/28.04, 28.05, 73/863.21–863.23, 863.25, 864.91, 865.5; 435/30, 34, 39; 96/413, 416

(56) References Cited

U.S. PATENT DOCUMENTS

| | | | |
|---|---|---|---|
| 3,498,027 A | | 3/1970 | Buchtel |
| 3,686,835 A | | 8/1972 | Strange et al. |
| 3,966,439 A | | 6/1976 | Vennos |
| 4,054,491 A | * | 10/1977 | Lindgren |
| 4,544,386 A | | 10/1985 | Trayford, III et al. |
| 4,942,774 A | | 7/1990 | McFarland |
| 4,963,167 A | | 10/1990 | Young |
| 5,205,155 A | | 4/1993 | Cooper |
| 5,574,230 A | * | 11/1996 | Baugh |
| 5,831,182 A | | 11/1998 | Swenson |
| 5,874,237 A | * | 2/1999 | Hull et al. |

FOREIGN PATENT DOCUMENTS

| | | |
|---|---|---|
| EP | 0 326 688 A2 | 5/1989 |
| EP | 0 428 850 A1 | 5/1991 |
| EP | 0 450 850 A2 | 10/1991 |
| GB | 1 430 531 | 3/1976 |
| GB | 2 098 087 A | 11/1982 |
| GB | 2214449 A | 9/1989 |
| GB | 2 224 118 A | 4/1990 |
| JP | 4-143632 | 5/1992 |
| WO | WO 86/02160 | 4/1986 |

OTHER PUBLICATIONS

Takamichi et al., "Determination Unit for Drug–Resistant Staphylococcus", First Page—Windows, Document: JP6113817, Apr. 1994.

Osamu et al., "Inspection Apparatus for Microorganism in Liguid", First Page—Windows, Document: JP1312991, Dec. 1989.

Search Report, GB 9913445.4, Claims Searched: 33–39, Date of Search: Dec. 14, 1999.

Search Report, GB 9913445.4, Claims Search: 1–16, 18, 19–29 & 33, Date of Search: Aug. 24, 1999.

Search Report Under Section 17 for GB 0013865.1; Date of Search: Nov. 14, 2000.

* cited by examiner

Primary Examiner—Robert Raevis
(74) Attorney, Agent, or Firm—Leydig, Voit & Mayer, Ltd.

(57) ABSTRACT

A gas sampling assembly takes a sample of a gas and passes the gas through a monitoring unit. A material within the unit removes particulates from the gas and a port is provided for feeding into the unit a material for indicating the presence of particulates. A transparent portion of the unit allows the indication to be viewed. The unit can be used in sterile packaging apparatus.

21 Claims, 4 Drawing Sheets

GAS SAMPLING ASSEMBLIES

BACKGROUND TO THE INVENTION

1. Field of the Invention

The invention relates to gas sampling assemblies and to air supply systems incorporating such assemblies and sterile packaging apparatus including such air supply systems.

2. Brief Review of the Prior Art

There are many circumstances where gas from a gas stream is flowed through a tube from a source to means utilizing the gas and where the gas may contain unwanted contamination in the form, for example, of microorganisms. An example of this is sterile packaging apparatus such as blow/fill/seal apparatus where the gas is air and is used to prevent contamination in the sterile packaging of product such as sterile liquids. Plainly, the presence in the air of contaminants such as micro-organisms can compromise the sterility of the packaging process and may result in packaged product being contaminated.

In order to remove contamination, the air supply is normally filtered through a filter (such as an HEPA filter (a high efficiency particulate-free air filter) or 0.2 μm rated filter) having a rating sufficient to remove unwanted particulate contaminants such as micro-organisms. The filter can be inspected at the end of its life to see whether its integrity has been compromised to allow contaminants to enter the air stream supplied to the apparatus. This procedure may, however, render a large quantity of the articles unusable if it is found that the filter integrity has been compromised, since it is not possible to say when during the life of the filter the compromise occurred so making it necessary to remove all articles produced during the life of the filter.

In order to try and overcome this problem, it has been proposed to include a sampling assembly comprising a sampling port in the form of a pipe extending through a wall of the tube normal to the length of the tube. The assembly also includes a monitoring unit connected to the port and containing filter material which filters out contaminants in a sample airstream taken from the port. At intervals, the port is closed and the unit removed so that any contaminants on the filter material can be identified. In the case of biological materials, this may be done by removing the filter material from the unit, placing the material in a dish and then culturing any biological materials present. If culturing shows an unacceptable level of contaminants is present, the batch of articles produced with a contaminated airstream can be identified and removed.

It is a problem with a monitoring unit of this known type that the steps necessary to culture the biological materials can themselves introduce contamination on to the filter material. This can occur, for example, in transferring the filter material from the filter unit to the location at which culturing takes place. The culturing may therefore give a "false positive" by indicating the presence of contamination when, in fact, no contamination is present in the airstream, the indication arising from handling of the medium in the culturing steps. This can lead to articles being considered contaminated when this is not, in fact, the case.

SUMMARY OF THE INVENTION

According to another aspect of the present invention, there is provided a gas sampling assembly comprising a device for sampling a flow of gas and a sterile gas monitoring unit. An inlet tube may lead from the sampling device for passing sampled gas from the sampling device. The sterile gas monitoring unit may include a sterile inlet, a sterile material, and a port. The sterile inlet may be provided on the monitoring unit and may be connected to the inlet tube for supplying sampled gas to the monitoring unit. The sterile material may be within the monitoring unit for removing contaminants from the sampled gas. The port may be provided on the monitoring unit. The assembly may further comprise a first sterile closure and a second sterile closure. The first sterile closure may close the sterile inlet on completion of the passage of sampled gas to the monitoring unit. The second sterile closure may close the port and may be removable to allow the sterile supply to the sterile material of a material indicating the presence of particulates. The sterile gas monitoring unit may further include a transparent portion on the monitoring unit for viewing the indication produced by the indicating material.

In some embodiments, the invention may operate in accordance with a method of identifying the presence of particulate contaminants in a sample of gas from a gas stream comprising passing said gas sample through a monitoring unit, collecting particulate contaminants in said monitoring unit and then supplying to said monitoring unit a material for indicating the presence of said particular contaminant.

By culturing the material in situ, the chances of false positive results are minimized.

The following is a more detailed description of some embodiments of the invention, by way of example, reference being made to the accompanying drawings in which:

DESCRIPTION OF THE PREFERRED EMBODIMENTS

Figure 1:
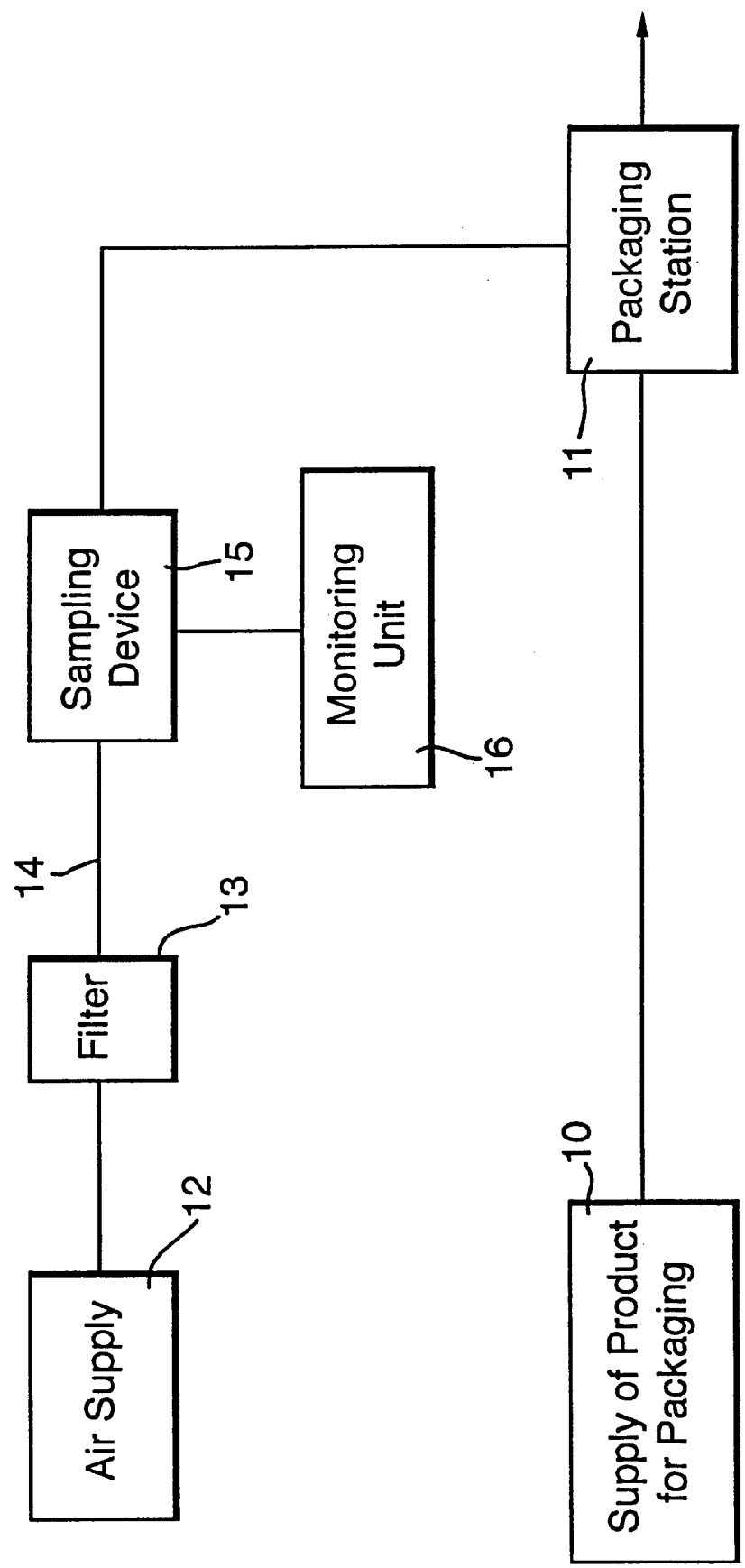
FIG. 1 is a schematic view of a sterile packaging apparatus incorporating a sampling device and a contamination monitoring unit.

Referring first to FIG. 1, the monitoring unit will be described in the context of its use in a sterile packaging apparatus in the form of a blow/fill/seal apparatus. It will be appreciated, however, that the monitoring unit can be used in other apparatuses and the following description is by way of example only.

Referring to FIG. 1, the blow/fill/seal apparatus includes a supply 10 of product to be packaged which may typically be a sterile liquid. The product is fed to a packaging station 11 where a plastics material is blown into an appropriately shaped packaging, such as a bottle, product, such as a sterile liquid, is fed to the packaging and is then sealed in the packaging.

The blowing, filling and sealing must take place in a sterile atmosphere and, for this purpose, air is supplied to the packing station 11 from an air supply 12. Air from the supply 12 is fed to an appropriately rated filter 13 which removes particulate contaminants in the air. For example, the filter may have an absolute rating of 0.2 μm Alternatively, the filter 13 may be a high efficiency particulate-free air (HEPA)

filter of the kind sold by Pall Corporation and formed by an acrylic copolymer on a non-woven support having a 99.97% retention of 0.3 µm DOP aerosol in gas/air filtration. From the filter 13, filtered air is supplied through a tube 14 to the packaging station 11.

A sampling device 15 is inserted in the tube 14 and feeds a sample of the air to a monitoring unit 16, to be described in detail below, which is used to test for the presence of culturable contaminants in the airstream. The sampling device 15 may be of conventional port type or may be as described in our UK patent application No. 9913443.9, the United States cognate of which was filed by Tallentire and Sinclair on Jun. 8, 2000 and entitled Sampling Devices. Testing takes place at predetermined time intervals which are correlated with the production of packaged articles from the packaging station 11 so that if contamination appears, it is known which batch of articles has been packaged using contaminated air.

Figure 2:
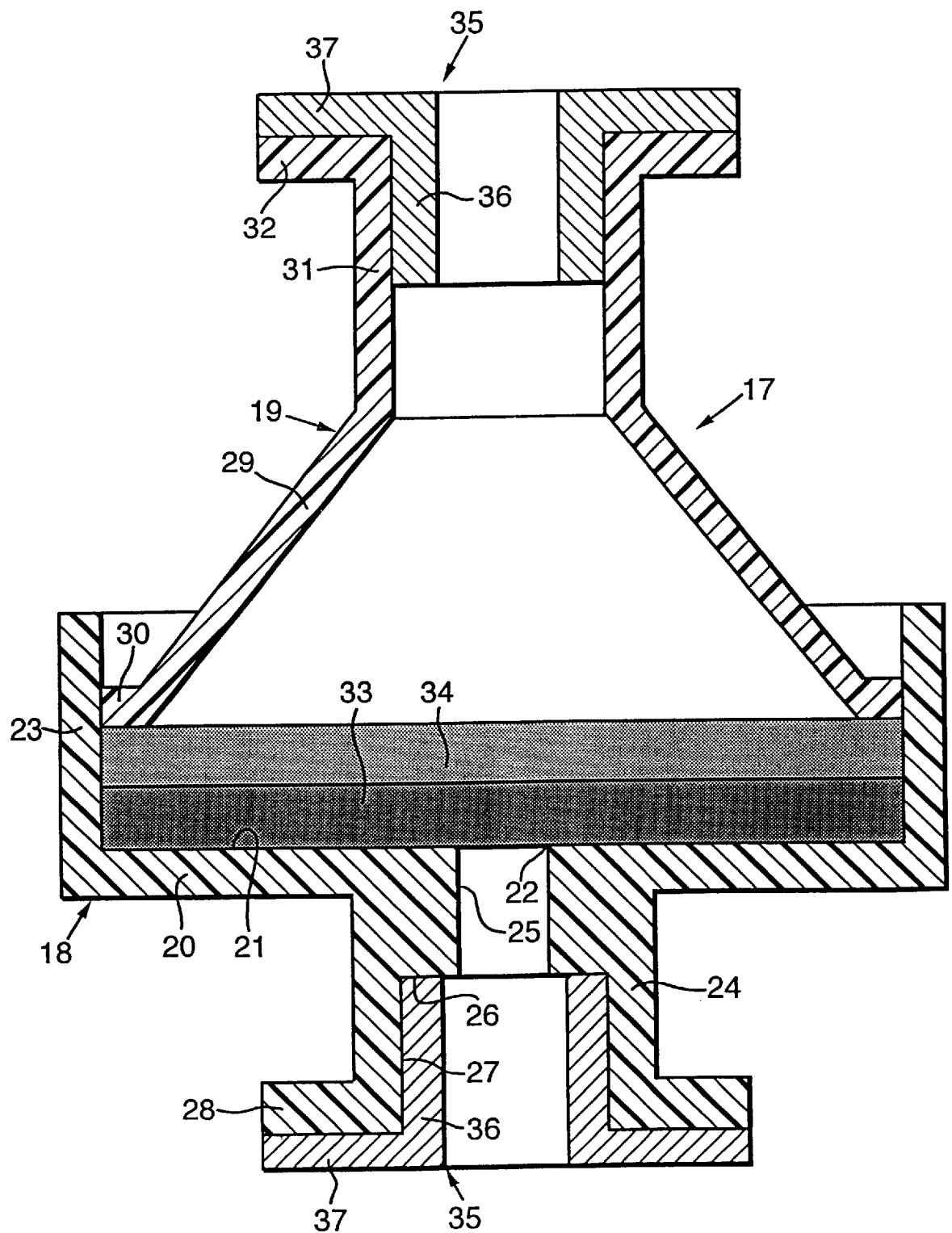
FIG. 2 is a cross section of a monitoring unit for use in the apparatus of FIG. 1, FIGS. 3a, 3b and 3c show three successive stages in the use of the monitoring unit of FIG. 2 to culture culturable biological material and also shows a sterile closure and an ampoule of sterile broth for use in the monitoring unit.

Referring next to FIG. 2, the monitoring unit 16 comprises a housing indicated generally at 17 formed by a base indicated generally at 18 and a cover indicated generally at 19 and overlying the base. The base 18 includes an annular floor 20 having a planar upper surface 21. The center of the floor is provided with an aperture 22. An annular wall 23 is upstanding around the outer periphery of the floor 20. An outlet 24 extends downwardly from the aperture and has an initial smaller diameter portion 25 connected via a step 26 to a larger diameter portion 27. An annular flange 28 extends around the end of the larger diameter portion 27 and lies in a plane generally normal to the axis of the outlet 24.

The cover 19 includes a frusto-conical portion 29 formed with an outwardly directed annular rib 30 at its wider diameter end and with a tubular inlet 31 of circular cross section extending from the narrower diameter end. The inlet 31 terminates in an outwardly directed flange 32 lying in a plane generally normal to the axis of the inlet 31.

The axis of the inlet 31 and the axis of the outlet 24 are coaxial and the diameter of the larger diameter portion 27 of the outlet 24 is substantially the same as the diameter of the inlet 31.

The rib 30 at the end of the larger diameter portion of the cover 19 is connected to the wall 23 of the base 18 at a location on the wall 23 spaced upwardly from the floor 20. The cover 19 is made from a transparent plastics material so making the frusto-conical portion 29 transparent.

The base 18 may also be moulded from a suitable plastics material whether transparent or otherwise. The housing 17 as a whole is sterilizable.

The floor 20 of the base 18 is covered by a disc-shaped absorbent pad 33. This may be of any suitable material but will usually be of fibres. Overlying the absorbent pad 33 is a disc of filter material 34. This may be a membrane or a fibrous material having a rating suitable for removing from an airstream passing through the housing 17 contaminants which are to be cultured. For example, the filter material 34 may have an absolute rating of 0.2 µm. As seen in FIG. 2, the dimensions of the absorbent pad 33 and the filter material 34 and the connection of the cover 19 to the base 18 are such that the rib 30 at the larger diameter end of the cover 19 locates on the periphery of the filter material 34 and holds the filter material 34 in position. Both the outlet 24 and the inlet 31 carry a respective moulded gasket 35. Each gasket 35 comprises an annular tubular body 36 and a flange 37 extending radially outwardly from an end of the tubular body. The gasket 35 in the outlet 24 has the tubular body 36 received in the larger diameter portion 27 with the gasket flange 37 covering the lower end of the outlet flange 28. The inlet gasket 35 has the tubular body 36 received in the inner surface of the inlet 31 and the gasket flange 37 covering the upper surface of the inlet flange 32.

Figure 3A:
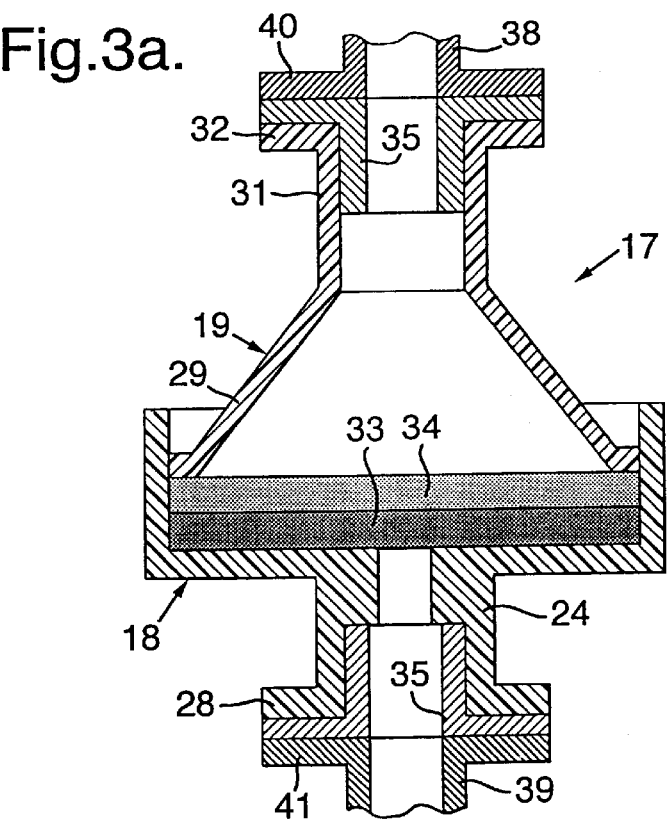
Figure 3B:
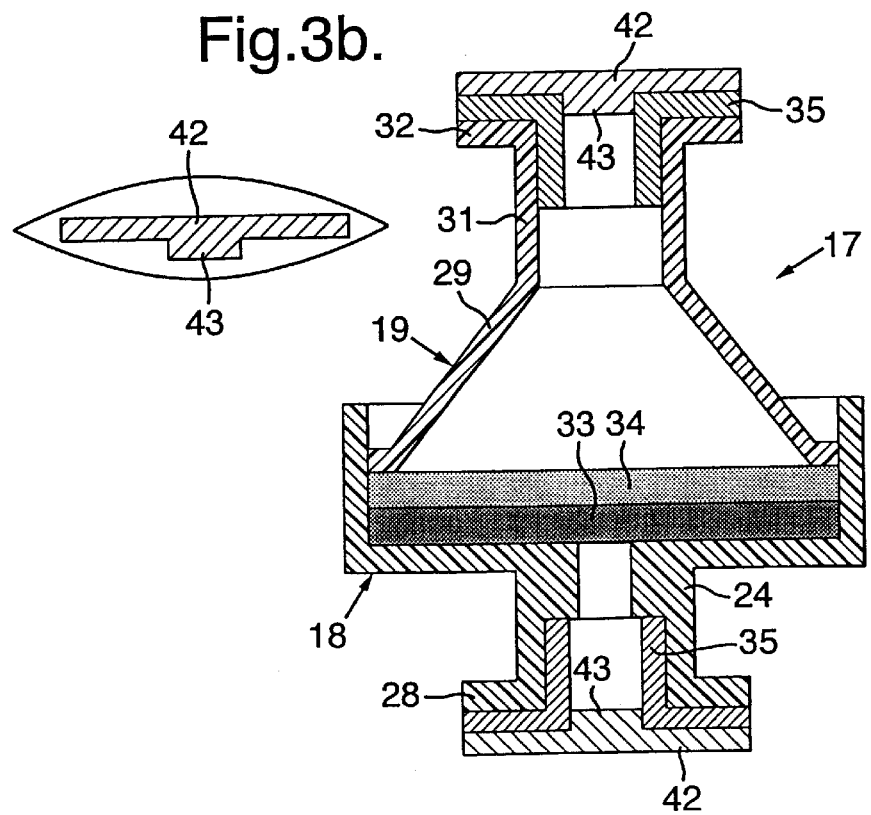
Figure 3C:
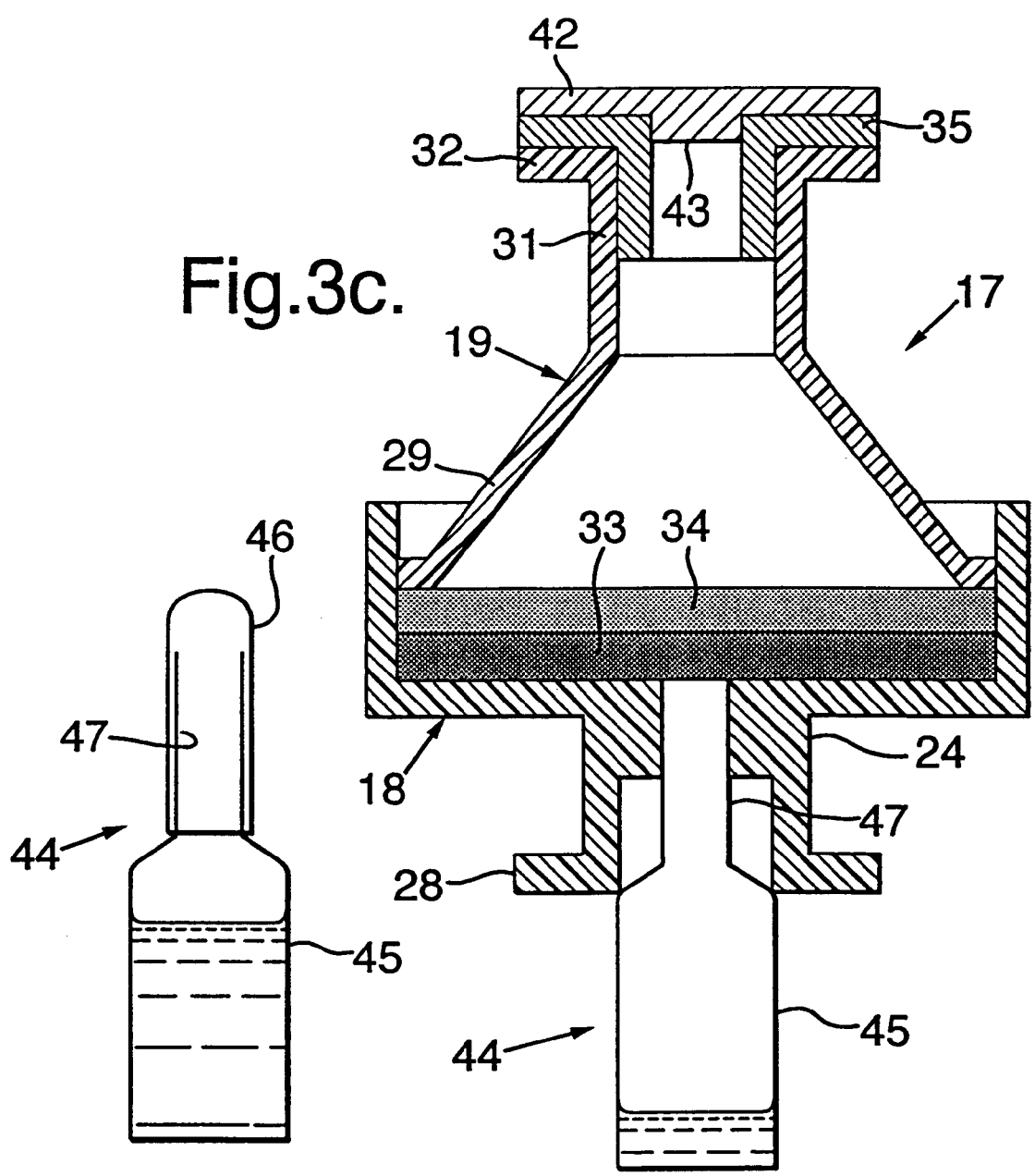

Referring next to FIGS. 3a, 3b and 3c, the monitoring unit 16 of the kind described above with reference to FIG. 2 is connected between an inlet tube 38 and an outlet tube 39 leading from the sampling device 15. As seen in FIG. 3a, the free end of the inlet tube 38 is provided with a flange 40 and the free end of the outlet tube 39 is also provided with a flange 41. The sampling unit 16, which has been previously sterilized, is fitted with gaskets 35 as described above and then has the outlet 24 connected to the outlet tube 39 and the inlet 31 connected to the inlet tube 38 via the respective flanges 28,41 and 32,40. The outlet tube 39 may be connected to a source of suction (not shown).

Air from the sampling device 15 is drawn into the monitoring unit through the inlet tube 38 and into the interior of the housing where it passes through the filter material 34 and the absorbent pad 33 before exiting via the outlet 24 and the outlet tube 39.

If the air contains contaminants, particularly biological contaminants, these will be held by the filter material 34.

After a predetermined time, the flow of air through the sampling unit 16 is halted. The sampling unit 16 is then disconnected from the inlet tube 38 and the outlet tube 39 and the outlet 24 and the inlet 31 are then capped using a sterile closure 42 seen in FIG. 3b. Referring to that Figure, the sterile closure 42 comprises a disc of sterilizable material with a depending annular projection 43. As seen in FIG. 3, the projection fits into the tubular body 36 of the moulded gaskets 35 covering the ends of the outlet 24 and the inlet 3 1. This ensures that no contamination enters the sampling unit 16 after disconnection.

The sampling unit 16 is then taken to the testing station. There, an ampoule 44 is brought to the sampling unit 16. As seen in FIG. 3c, the ampoule 44 comprises a flexible container 45 closed by a cap 46. The ampoule 44 contains a sterile broth for incubating biological material such as micro-organisms held by the filter material 34.

At the testing station, the outlet 24 is uncovered by removal of the associated sterile closure 42 and the associated gasket 35. The removal of the gasket 35 uncovers the sterile surface of the outlet beneath the gasket 35. The open end 47 of the container 45 is dimensioned to fit tightly into the smaller diameter portion 25 of the outlet 24 once the cap 46 has been removed, as seen in FIG. 3. The ampoule 44 can then be squeezed to transfer the contents of the ampoule 44 into the housing 17. The broth in the ampoule 44 initially contacts the absorbent pad 33 which acts to spread the broth across the whole area of the filter material and to hold the broth in contact with the filter material 34. The tightness of the fit of the ampoule 44 allows the ampoule 44 to be left in position after insertion to ensure that no contamination enters the housing.

The broth is then left to incubate any biological material such as micro-organisms on the filter material. After an appropriate time, this can be viewed through the transparent frusto-conical portion 29 of the cover 19 and the presence of any biological material such as micro-organisms determined.

Of course, in the interim, a further monitoring unit 16 is inserted between the inlet tube 38 and the outlet tube 39.

It will be appreciated that there are a number of alterations that may be made to the sampling unit 16 described above. The housing 17 described above need not have the form shown; it could have any suitable shape. The presence of the absorbent pad 33 is optional; and the filter material 34 itself may act to hold and spread the broth satisfactorily. The moulded gaskets 35 may be removed after removal of the sampling unit 16 from the inlet tube 38 and the outlet tube 39 and before closure by the sterile closures 42 in order to remove any contamination from the inlet and outlet tubes 38,39. In this case, the projection 43 on the sterile closures 42 may be of larger diameter to fit in the outlet 24 and the inlet 31 rather than in the tubular body 36 of the moulded gaskets 35.

Although the broth from the ampoule 44 is shown entering the housing 17 from the outlet 24, it could enter through the inlet 31 or through another aperture provided in the housing 17. The filter material 34 need not be formed by a single layer of material; it could be formed by a number of layers of material. The fluid in the ampoule 44 need not be such as to indicate the presence of microorganisms. It could be such as to indicate the presence of other biological material or even non-biological material.

The sampling unit need not be used in sterile packaging apparatus; there may be other applications where the sampling unit may be utilized.

What is claimed is:

1. A gas sampling assembly comprising:
   a device for sampling a flow of gas;
   an inlet tube leading from the sampling device for passing sampled gas from the sampling device;
   a sterile gas monitoring unit, including
      a sterile inlet provided on the monitoring unit and connected to the inlet tube for supplying sampled gas to the monitoring unit;
      a sterile material within the monitoring unit for removing particulates from said sampled gas, and
      a port provided on the monitoring unit,
   a first sterile closure for closing the sterile inlet on completion of passage of sampled gas to the monitoring unit; and
   a second sterile closure for closing the port, the sterile closure being removable to allow a sterile supply to the sterile material of a material indicating the presence of particulates; and
   the sterile gas monitoring unit further including a transparent portion on the monitoring unit for viewing the indication produced by the indicating material.

2. An assembly according to claim 1 wherein the sterile gas monitoring unit comprises a housing with said sterile material being held in said housing, a part of the housing being transparent to provide said transparent portion.

3. An assembly according to claim 2 wherein the sterile material is a filter material.

4. An assembly according to claim 2 wherein the housing includes a base on which the sterile material rests and a cover overlying the base, the transparent portion being provided in said cover.

5. An assembly according to claim 2 wherein the housing includes a base on which the sterile material rests and a cover overlying the base, the transparent portion being provided on the cover and the sterile inlet being formed in the cover with the port leading from the base.

6. An assembly according to claim 5 wherein the cover includes a frusto-conical portion having a wider end and a narrower end, the wider end being connected to the base and the narrower end leading to said sterile inlet.

7. An assembly according to claim 5 wherein the base includes a planar surface for supporting the sterile material and the port includes an outlet passage extending said surface in a direction generally normal to said surface.

8. An assembly according to claim 7 wherein the passage includes a first portion of smaller cross-sectional area closer to the surface and a second portion of larger cross-sectional area further from the surface.

9. An assembly according to claim 8 wherein the second portion is covered by the second sterile closure.

10. An assembly according to claim 1 wherein the sterile inlet includes means forming a joint with the inlet tube.

11. An assembly according to claim 10 wherein said joint includes a flange extending around said inlet.

12. An assembly according to claim 10 wherein the joint includes a gasket.

13. A sterile packaging apparatus including a gas sampling assembly according to claim 1.

14. A gas sampling assembly for monitoring the contaminant level in a flow of a gas comprising:
    a device for supplying a sample of the gas and including a sample port or outlet for providing the gas sample and
    a gas monitoring unit fluidly communicating with the sampling device to supply the gas sample to the gas monitoring unit, the gas monitoring unit including
       a housing having
       a sterile inlet coupled to the outlet of the sampling device,
       a sterile interior which receives the gas sample from the sterile inlet,
       a sterile material within the gas monitoring unit for removing contaminants from the sampled gas, wherein the sterile interior is defined between the sterile inlet and the sterile material,
       a port for providing a sterile supply of an indicating material to the sterile material to indicate the presence of contaminants, and
       a transparent portion on the gas monitoring unit for viewing an indication produced by the indicating material.

15. The gas sampling assembly according to claim 14, wherein the port comprises an outlet port of the housing and the gas monitoring unit includes a removable gasket coupled to the outlet port.

16. The gas sampling assembly according to claim 14, wherein the gas monitoring unit fluidly communicates with the sampling device via an inlet tube.

17. The gas sampling assembly according to claim 14, wherein the sterile material comprises a filter material.

18. The gas sampling assembly according to claim 14, wherein the housing includes a base on which the sterile material rests and a cover overlying the base, the transparent portion being provided in said cover.

19. The gas sampling assembly according to claim 14, wherein the housing includes a base on which the sterile material rests and a cover overlying the base, the transparent portion being provided on the cover, the sterile inlet being formed in the cover and the port comprising an outlet port leading from the base.

20. The gas sampling assembly according to claim 19, wherein the base includes a planar surface for supporting the sterile material and wherein the port comprises an outlet port including an outlet passage extending from said surface in a direction normal to said surface.

21. The gas sampling assembly according to claim 20, wherein the passage includes a first portion of smaller cross-sectional area closer to the surface and a second portion of larger cross-sectional area further from the surface, wherein the second portion is capable of receiving a sterile closure.

* * * * *